United States Patent [19]

Crenshaw et al.

[11] 4,171,363

[45] Oct. 16, 1979

[54] 1,2,3-THIADIAZOLE PROCESS

[75] Inventors: Ronnie R. Crenshaw, Dewitt; Richard A. Partyka, Liverpool, both of N.Y.

[73] Assignee: Bristol-Myers Company, New York, N.Y.

[21] Appl. No.: 906,888

[22] Filed: May 17, 1978

Related U.S. Application Data

[62] Division of Ser. No. 770,966, Feb. 22, 1977, Pat. No. 4,101,548.

[51] Int. Cl.$^2$ ............................................. A61K 31/505
[52] U.S. Cl. ................................... 424/251; 544/284; 544/293
[58] Field of Search ............................................. 424/251

[56] References Cited

U.S. PATENT DOCUMENTS

| 3,511,836 | 5/1970 | Hess | 544/291 |
|---|---|---|---|
| 3,517,005 | 6/1970 | Cronin et al. | 544/293 |
| 3,594,480 | 7/1971 | Cronin et al. | 55/207 |
| 3,635,979 | 1/1972 | Hess et al. | 544/291 |
| 3,663,706 | 5/1972 | Hess | 424/251 |
| 3,669,968 | 6/1972 | Hess | 544/291 |
| 3,769,286 | 10/1973 | Hess | 424/251 X |
| 3,780,040 | 12/1973 | Schnettler et al. | 544/292 |
| 3,812,127 | 5/1974 | Cronin et al. | 544/363 |
| 3,920,636 | 11/1975 | Takahashi et al. | 542/439 |
| 4,001,237 | 1/1977 | Partyka | 424/251 X |
| 4,001,238 | 1/1977 | Partyka et al. | 424/251 X |

OTHER PUBLICATIONS

Chem. Abs., vol. 78, 1973, p. 480, Ab. No. 72180s.

*Primary Examiner*—Anna P. Fagelson
*Attorney, Agent, or Firm*—Robert H. Uloth

[57] ABSTRACT

A series of novel 4-amino-2-(thiadiazole-carbonyl piperazinyl)-6,7-dimethoxyquinazolines is disclosed having antihypertensive properties. The thiadiazole substituent may be optionally substituted with alkyl or lower alkoxy carbonylamino groups. A representative embodiment of the invention is 4-amino-6,7-dimethoxy-2-[4-(5-ethoxy-carbonylamino-1,2,3-thiadiazole-4-carbonyl)-piperazin-1-yl]-quinazoline.

3 Claims, No Drawings

1,2,3-THIADIAZOLE PROCESS

CROSS-REFERENCE TO RELATED APPLICATION

This application is a division of Ser. No. 770,966, filed Feb. 22, 1977, and now U.S. Pat. No. 4,101,548.

BACKGROUND OF THE INVENTION

1. Field of the Invention

This invention provides quinazoline compounds and pharmaceutically acceptable acid addition salts thereof having antihypertensive utility. In particular, the instant invention relates to novel 1,2,3-thiadiazole-carbonyl piperazinyl quinazolines which are potent and long acting antihypertensive drugs.

2. Description of the Prior Art

U.S. Pat. Nos. 3,511,836, 3,635,979, and 3,663,706 disclose various 4-amino-6,7-dimethoxy-2-[4-(heterocyclic-2-carbonyl)-piperazin-1-yl]-quinazolines. One of these compounds, i.e., 2-[4-(2-furoyl)-piperazin-1-yl]-4-amino-6,7-dimethoxyquinazoline described in Example LXXII of these patents is a clinically useful antihypertensive agent and is marketed as such in many countries of the world under the generic name prazosin. It is considered that the antihypertensive efficacy of prazosin results from a dual mechanism of action: (i) a direct peripheral vasodilation effect on vascular smooth muscle, and (ii) a functional peripheral α-adrenergic receptor blockade, H. Adriaensen, *The Practitioner*, 214, 268 (1975); Mroczek, et al., *Current Therapeutic Research*, 16, 769 (1974); Scriabine, et al., *Experimentia*, 24, 1150 (1968); Constantine, et al., "Hypertension: Mechanisms and Management", ed. by Onesti, Kim and Moyer; Grune and Stratton, 1973 pp. 429–44; and Zacest, *Med. J. of Austral. Special Supplement*, 1, 4 (1975). Although initial clinical assessments on prazosin indicated a low incidence of side effects, recent reports have revealed severe adverse reactions of postural hypotension in some patients, Bendall, et al., *Brit. Med. J.*, 727 (June 29, 1975); Rees, *Brit. Med. J.*, 593 (Sept. 6, 1975); Gabriel, et al., The Lancet, 1095 (May 10, 1975); and Bloom, et al., *Current Therapeutic Research*, 18, 144 (1975). It is believed that this type of side effect results from the α-blockade component of prazosin. Indeed, it has been stated by R. Zacest in the *Med. J. of Austral., Special Supplement*, 1, 4 (1975) that "if the alpha adrenergic 'blocking' activity does prove to be significant with high doses it may lead to postural hypotension".

U.S. Pat. Nos. 3,669,968 and 3,769,286 cover trialkoxyquinazolines, such as those having the formula

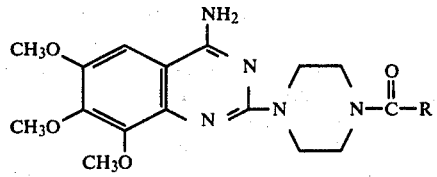

wherein R may be a number of different groups including furyl and thienyl. These patents claim to have certain advantages over the corresponding 6,7-dialkoxy compounds such as those disclosed in the patents previously discussed. Thus, it is stated that such compounds "have a more favorable pharmacological profile (e.g., they are non-adrenolytic in dogs) and possess greatly improved solubility characteristics (particularly in water) as contrasted to the corresponding 6,7-dialkoxy compounds reported in the prior art". One of the compounds disclosed in these patents is known by the generic name trimazosin and has the formula

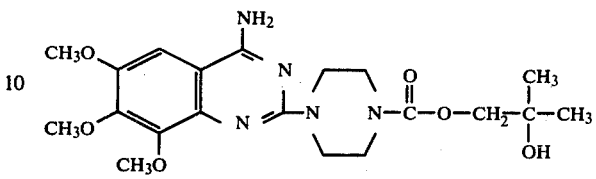

Trimazosin is reported to be active in humans as an antihypertensive agent, DeGuia, et al., *Current Therapeutic Research*, 15, 339 (1973); Vlachakis, et al., *Current Therapeutic Research*, 17, 564 (1975). However, it is a much weaker drug than prazosin, the respective clinical daily dose ranges being approximately 150 to 500 mg. for trimazosin as compared to 1.5 to 15 mg. for prazosin.

U.S. Pat. Nos. 3,517,005, 3,594,480, and 3,812,127 describe certain piperazinyl quinazolines having both bronchodilator and antihypertensive activity, e.g., a compound having the formula

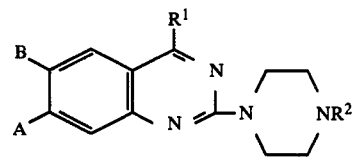

wherein A and B may each be alkoxy, etc., $R^1$ may be hydrogen or alkyl and $R^2$ may be hydrogen or a radical such as alkyl, benzoyl, etc.

U.S. Pat. No. 3,920,636 describes homopiperazino quinazolines as antihypertensive agents, e.g., the compound

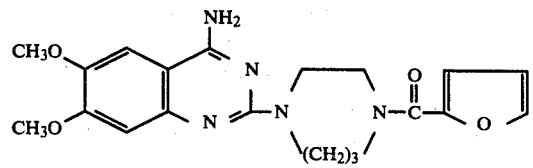

U.S. Pat. No. 4,001,238 discloses 1,2,4-oxadiazole amides useful as antihypertensive agents characterized by the formula

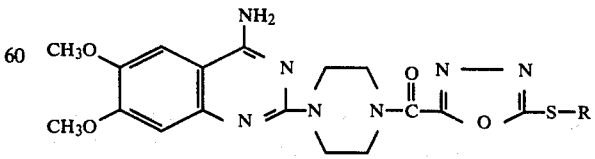

in which R is (lower)alkyl.

U.S. Pat. No. 4,001,237 describes compounds having antihypertensive utility characterized by the formula

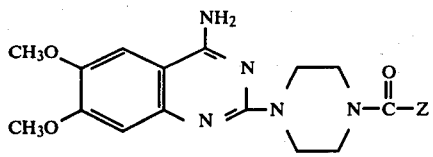

wherein Z is an oxazole, isoxazole, thiazole and isothiazole radical.

U.S. Pat. No. 3,780,040 discloses compounds useful as antihypertensive agents such as the compound

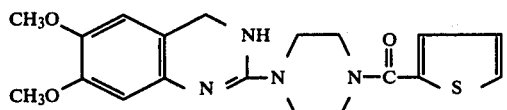

Netherlands application No. 72 06,067 (CA, 78, 72180s) describes a process for preparing aminoquinazolines, such as prazosin, by treating the corresponding o-aminobenzonitrile in the presence of phenyl lithium according to the following mechanism

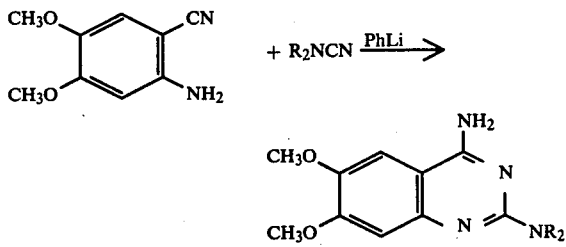

wherein $R_2N$ may be the group 4-(2-furoyl)-1-piperazinyl.

SUMMARY OF THE INVENTION

This invention is concerned with new quinazoline compounds, and to a process for their preparation. The quinazolines possess valuable pharmacologic properties and another aspect of this invention relates to an antihypertensive process utilizing the new compounds. More particularly, the invention is especially concerned with 1,2,3-thiadiazolecarbonyl-2-piperazinyl-6,7-dimethoxyquinazolines characterized by Formula I

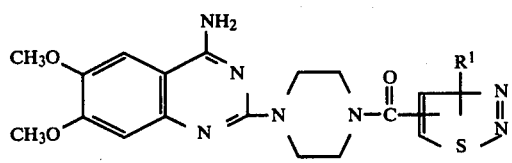

and pharmaceutically acceptable acid addition salts thereof wherein $R_1$ is hydrogen, lower alkyl, $NH_2$ or $NHCO_2R_2$ in which $R_2$ is lower alkyl.

Other contemplated classes of compounds following within the ambit of Formula I are those wherein the thiadiazole radical

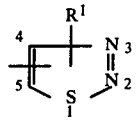

is defined as:

(1) attached in the 4- or 5-ring position to the carbonyl functionality and $R_1$ is hydrogen;

(2) attached in the 4- or 5-ring position to the carbonyl functionality and $R_1$ is lower alkyl;

(3) attached in the 4- or 5-ring position to the carbonyl functionality and $R_1$ is methyl;

(4) attached in the 4-ring position to the carbonyl functionality and $R_1$ is amino;

(5) attached in the 5-ring position to the carbonyl functionality and $R_1$ is amino;

(6) attached in the 4-ring position to the carbonyl functionality and $R_1$ is $NHCO_2R_2$ in which $R_2$ is lower alkyl;

(7) attached in the 5-ring position to the carbonyl functionality and $R_1$ is $NHCO_2R_2$ in which $R_2$ is lower alkyl;

(8) attached in the 4-ring position to the carbonyl functionality and $R_1$ is $NHCO_2R_2$ in which $R_2$ is methyl;

(9) attached in the 5-ring position to the carbonyl functionality and $R_1$ is $NHCO_2R_2$ in which $R_2$ is methyl;

(10) attached in the 4-ring position to the carbonyl functionality and $R_1$ is $NHCO_2R_2$ in which $R_2$ is ethyl;

(11) attached in the 5-ring position to the carbonyl functionality and $R_1$ is $NHCO_2R_2$ in which $R_2$ is ethyl.

The preferred compound of this invention is 4-amino-6,7-dimethoxy-2-[4-(5-ethoxycarbonylamino-1,2,3-thiadiazole-4-carbonyl)-piperazin-1-yl]quinazoline. This compound has a long duration of action as illustrated in spontaneous hypertensive rats wherein a 22% reduction in systolic blood pressure is obtained 24 hours after administering an oral dose of 10 mg./kg. body weight.

The term "pharmaceutically acceptable" used herein to describe an acid addition salt of a compound of Formula I refers to those salts having anionic species of a variety of relatively non-toxic inorganic or organic acids. The anion does not contribute appreciably to the toxicity of the salt or to its pharmacological activity. Illustrative of such salts are those formed with acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzenesulfonic, p-toluenesulfonic, and related acids. Preparation of the mono-acid addition salts may be carried out in conventional manner by treating a solution or suspension of the free base in a reaction inert organic solvent with one chemical equivalent of the acid or if the di-acid addition salt is desired, at least two chemical equivalents of the acid. Conventional concentration or crystallization techniques are employed in isolating the salts.

It is to be understood that the term "lower alkyl" as used herein refers to alkyl radicals containing from 1 to 4 carbon atoms inclusive such as methyl, ethyl, propyl, isopropyl, n-butyl, sec-butyl, iso-butyl, and tert.butyl.

According to the present invention, compounds of Formula I are prepared by reacting a quinazoline derivative of Formula II

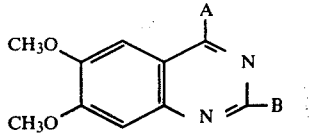

(II)

wherein substituent "A" is amino, or halogen (preferably chlorine or bromine) and substituent "B" is halogen (preferably chlorine or bromine), piperazino, lower alkylthio of 1 to 4 carbon atoms inclusive, $CH_3SO_3$, $F_3SO_3$, aryl $SO_3$ such as p-tolylsulfonate or a 1,2,3-thiadiazolecarbonylpiperazine radical

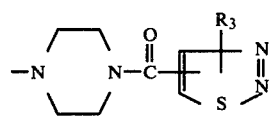

wherein $R_3$ is hydrogen, lower alkyl or $NHCO_2R_2$ (in which $R_2$ is lower alkyl) with a reactant of the group consisting of ammonia, compounds of Formula III and compounds of Formula IV

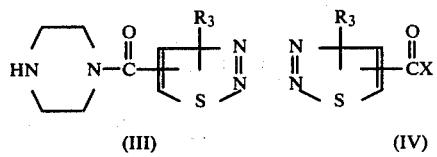

wherein $R_3$ is as defined above and "X" is a carbonyl activating group of the type typically used in amidation reactions such as halogen (preferably chlorine or bromine), azido, ethoxycarbonyloxy, 1-imidazo and the like in an aqueous or reaction inert organic solvent, to provide compounds of Formula Ia

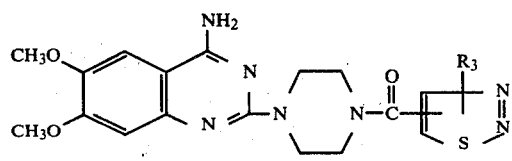

(Ia)

wherein $R_3$ is as defined above, and thereafter, if desired, hydrolyzing Formula Ia in which $R_3$ is $NHCO_2R_2$ to provide compounds of Formula I wherein $R_1$ is amino.

Equimolar amounts of Formula II and Formula III or Formula IV reactants are generally satisfactory, although, with ammonia, a substantial excess is preferred. The term "reaction inert solvent" as used herein refers to those organic solvents which themselves do not enter into the reaction such as tetrahydrofuran, dioxane, dimethylacetamide, dimethylformamide, and the like. When the reaction is complete, the solvent is removed by evaporation. The resulting residue (consisting of a salt of Formula I) stirred with a base such as ammonium hydroxide, sodium hydroxide, potassium hydroxide, sodium carbonate, potassium carbonate and then purified according to conventional techniques provides the Formula I free base which may be converted to a pharmaceutically acceptable salt by treating with an acid such as hydrochloric, hydrobromic, and the like.

The following reaction schemes of Equation 1-5 illustrate the various synthetic routes embodied in the preparation of the compounds of the instant invention according to the process discussed above.

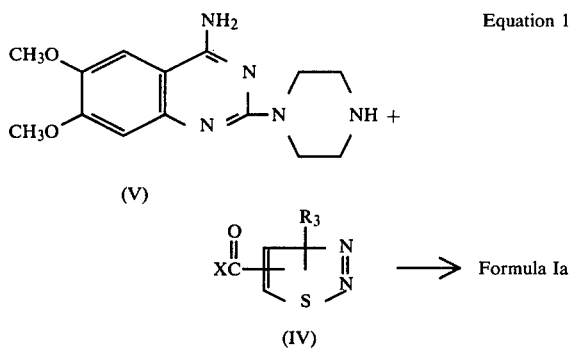

Equation 1

Equation 1 illustrates the preferred process exemplified in examples appearing hereinafter for preparation of compounds characterized by Formula Ia wherein $R_3$ is hydrogen, lower alkyl or $NHCO_2R_2$ in which $R_2$ is lower alkyl. Reaction of compound V with compounds characterized by Formula IV is preferably conducted in a reaction inert organic solvent at room temperature, with heating at reflux briefly to insure completion of the reaction. Representative reaction inert organic solvents which may be employed include ether, dioxane, benzene, toluene, acetonitrile, halogenated hydrocarbons such as chloroform, dimethylformamide, dimethylsulfoxide, and the like. At least a molar equivalent of the carbonyl halide reactant (IV) is employed and the reaction is stirred for a period of 1 to 24 hours following addition. The products of Formula Ia are filtered from the reaction mixture or isolated by conventional techniques such as evaporation of the solvent and recrystallization of the residue from alkanol solvents such as methanol, ethanol, isopropanol, chloroform or the like.

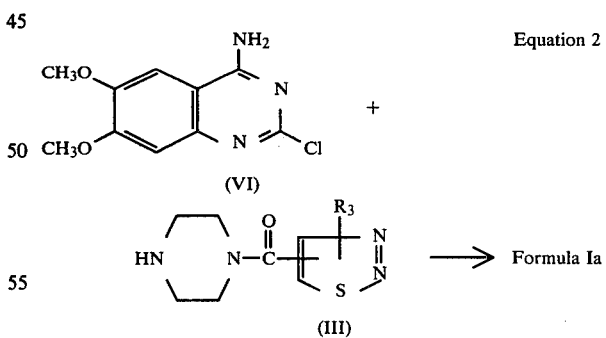

Equation 2

As depicted in Equation 2 above, 2-chloro-4-amino-6,7-dimethoxyquinazoline of Formula VI is reacted with a piperazine intermediate of Formula III wherein $R_3$ is as defined above, in an inert reaction solvent at elevated temperatures. The reaction is generally complete in a period of 16 hours at a temperature ranging from 150°-180° C. for periods of 1 to 48 hours.

Another method for the preparation of compounds of this invention involves the reaction sequence of Equation 3

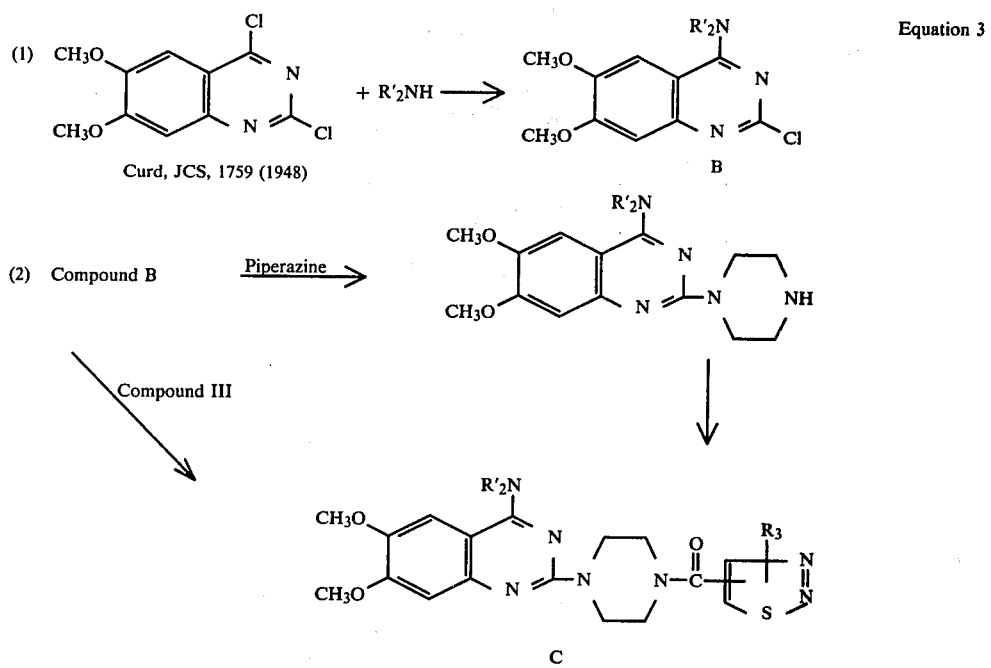

wherein R'$_2$ is a conventional amine protecting group (e.g., a t-butoxycarbonyl group) and wherein R$_3$ is as defined above. The amine protecting group may then be removed from compound C by conventional means to provide the desired product, compound Ia.

Another procedure for the preparation of Compounds of this invention is illustrated by the following reaction sequence of Equation 4

Equation 4

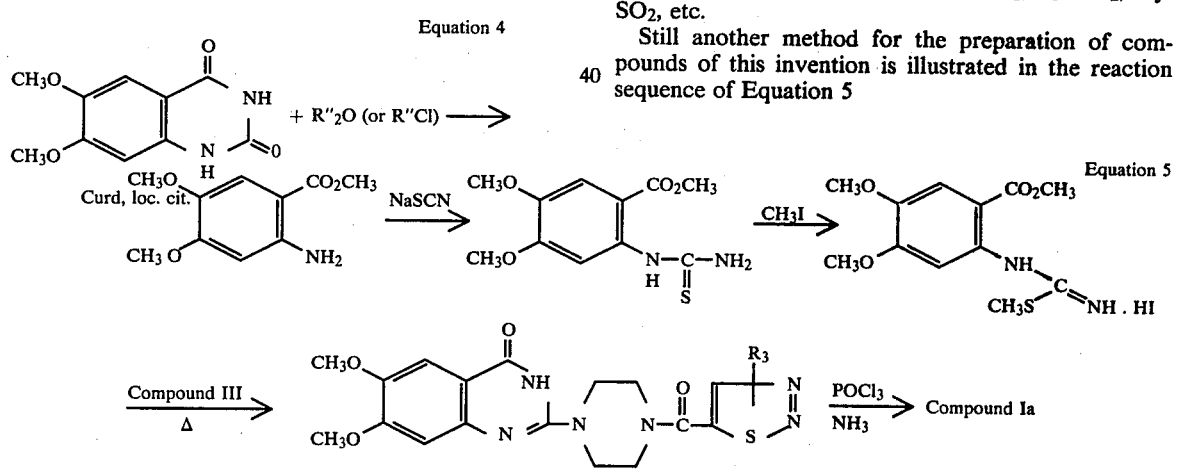

wherein R" is a group such as CH$_3$SO$_2$, F$_3$CSO$_2$, aryl SO$_2$, etc.

Still another method for the preparation of compounds of this invention is illustrated in the reaction sequence of Equation 5

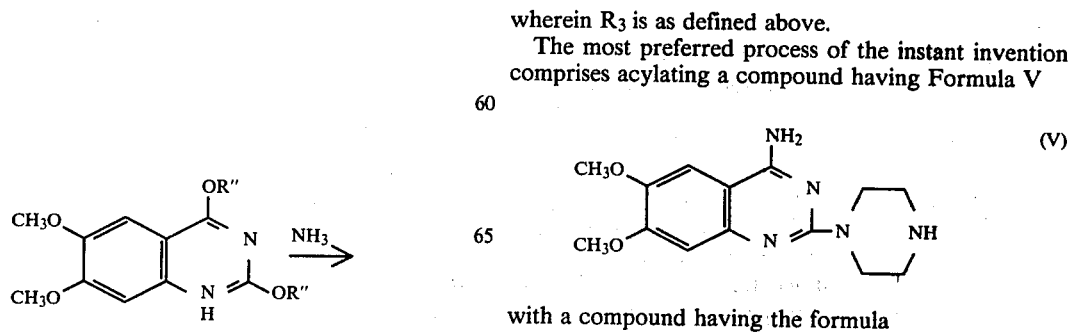

wherein R$_3$ is as defined above.

The most preferred process of the instant invention comprises acylating a compound having Formula V with a compound having the formula

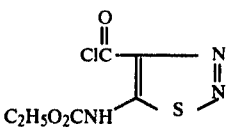

in dioxane to provide a product having the formula

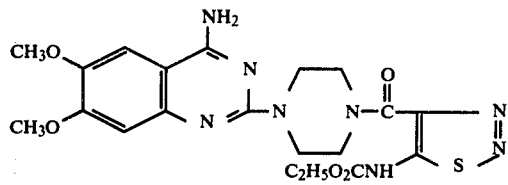

The efficacy of the compounds of this invention as antihypertensive agents was determined according to standard pharmacological test procedures. Results of tests for representative compounds of Formula I compared to prazosin are set forth in Table 1. As shown in Table 1, the products of Examples 1-3 have substantial antihypertensive potency comparable to prazosin with significantly less peripheral α-adrenergic blocking involvement. Thus, the compounds described and claimed in this application represent a significant and unexpected advance in the continuing quest for improved antihypertensive drugs with less potential for side effects as reflected by diminished α-adrenergic blocking activity.

In Table 1, antihypertensive activity was determined by oral administration to spontaneous hypertensive rats, the in vitro α-adrenergic receptor blocking effect was determined according to the following test method.

ISOLATED RAT SEMINAL VESICLE ASSAY

Dungan et al, *Int. J. Neuropharmacol.*, 4:219 (1965) have shown that the seminal vesicle of the rat is a tissue which is notably responsive to compounds which activate α-receptors but is relatively insensitive to compounds which activate β-receptors. Lietch et al, *Brit. J. Pharmacol.*, 9:236 (1954), have employed the isolated rat seminal vesicle in the comparative assay of α-receptor blocking drugs and the present studies were carried out using a modification of their procedure.

Male Long Evans rats weighing approximately 300 g. were sacrificed by a sharp blow on the head. Seminal vesicles were removed and transferred to a shallow disk containing modified Tyrode's solution. The vesicles were emptied of their contents by squeezing them gently with a pair of forceps. Silk thread (4-0) was attached to both ends of the vesicle and it was suspended in a 20 ml. muscle chamber containing modified oxygenated Tyrode's solution (g./liter: NaCl 8, KCl 0.2, CaCl$_2$ 0.26, NaHCO$_3$ 1, Na$_2$HPO$_4$ 0.0575, glucose 0.5 and MgCl$_2$ 0.02). The bathing fluid was maintained at 37° C. with a thermostatically controlled isolated organ tissue bath. Contractions were recorded isometrically by means of a force displacement transducer and recordings were made with a Beckman RP Dynograph. Norepinephrine (NE) was added to the muscle chamber in volumes ranging from 0.1 to 0.4 ml. with a one ml. syringe attached to a 3 inch 20 gauge needle. NE and test compounds were dissolved in deionized water.

NE response curves were obtained alone and in the presence of test compounds. NE was allowed to remain in contact with the strip until a maximal contraction was obtained. The strip was then washed with the perfusion fluid for 15-30 seconds and the preparation was allowed to return to base line before a subsequent dose of NE was given. Increasing amounts of NE were injected into the bath in the same manner until a complete dose response was obtained.

The seminal vesicles used to obtain the control NE dose response were discarded and new preparations were placed in the tissue bath for evaluation of the test compound. The test compound was added directly to the perfursion fluid (10 nanograms/ml.) and the strips were allowed to remain in contact with the bathing media for at least 10 minutes before the NE dose response was determined.

ED$_{50}$ values for NE were obtained by regression analysis as described by Finney, *Probit. Analysis,* 2d Ed., Cambridge (1964). A minimum of 4 strips and at least 4 doses were employed to calculate the regression lines. The ED$_{50}$ value is defined as the concentration of NE which produces a contraction equal to 50% of the maximal contraction.

The ratio of the α-adrenergic blocking activity of test compounds relative to that of prazosin was calculated as follows:

$$\% \text{ Change from } NE = \frac{ED_{50} + \text{test compound} - ED_{50} \, NE \text{ Alone}}{ED_{50} \, NE \text{ Alone}} \times 100$$

The value obtained for test compound was then expressed as a ratio of the value obtained for prazosin.

$$\text{Activity Ratio} = \frac{\% \text{ Change for } NE - \text{test compound}}{\% \text{ Change from } NE - \text{Prazosin}}$$

Table 1

Comparative Antihypertensive Effects in the Spontaneous Hypertensive Rat and Isolated Rat Seminal Vesicles

| | | Antihypertensive | | α-Adr. Bl. | |
|---|---|---|---|---|---|
| R | | ED$_{50}$ mm Hg (mg/kg.) | Activity Ratio (A) | Activity Ratio (B) | Ratio A/B |
| 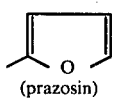 (prazosin) | | 2.1 | 1 | 1 | 1 |

Table 1-continued

Comparative Antihypertensive Effects in the Spontaneous Hypertensive Rat and Isolated Rat Seminal Vesicles

[Structure: 6,7-dimethoxyquinazoline with NH$_2$ group, connected through N to piperazinyl-N-C(=O)-R]

| R | Antihypertensive ED$_{50}$ mm Hg (mg/kg.) | Activity Ratio (A) | α-Adr. Bl. Activity Ratio (B) | Ratio A/B |
|---|---|---|---|---|
| C$_2$H$_5$O$_2$CNH-[thiadiazole] (Example 1) | 2.8 | 0.75 | 0.15 | 5.0 |
| [thiadiazole] (Example 2) | 4.0 | 0.53 | 0.27 | 2.0 |
| [thiazole] (Example 3) | 4.0 | 0.53 | 0.23 | 2.3 |

As previously discussed, compounds of the instant invention are valuable antihypertensive agents, possessing comparable antihypertensive potency to prazosin with significantly less peripheral α-adrenergic blocking properties. The compounds may be used in the form of the free base or in the form of pharmaceutically acceptable acid salts thereof and may be administered orally or parenterally with oral administration being preferred. Generally, dosages will range from 0.1 to 10 mg. 3 to 4 times per day per human adult. As is usual in antihypertensive therapy, the particular optimum dosage may vary considerably depending upon the sensitivty of the patient to the drug and the severity of the hypertension.

The process of the instant invention for treating hypertension is carried out by systemically administering to a mammal in need of such treatment such as those having hypertension or predisposed thereto an antihypertensive effective amount of a 2-piperazinyl-6,7-dimethoxyquinazoline characterized by Formula I or a pharmaceutically acceptable acid addition salt thereof. By systemic administration, it is intended to include both oral and parenteral routes. Examples of parenteral administration are intramuscular, intravenous, intraperitoneal, rectal, and subcutaneous administration. The dosage will vary with the form of administration and the particular compound chosen however, from about 0.001 to 3 milligrams per kilogram of body weight of the mammal of a 2-piperazinyl-6,7-dimethoxyquinazoline characterized by Formula I administered in effective single or multiple dosage units is generally satisfactory. In accordance with conventional clinical practice, an antihypertensive agent of Formula I is administred at a dosage substantially less than the dose of the compound which is thought to be effective. Thereafter, the dosage is increased by small increments until the optimum antihypertensive effect under the circumstances is reached. At effective antihypertensive dosage levels, the compounds of this invention are substantially free of those harmful or deleterious side effects generally associated with α-adrenergic blockade.

In carrying out the antihypertensive process, the active ingredient of Formula I and pharmaceutically acceptable acid addition salts thereof may be administered orally in such forms as tablets, dispersible powders, granules, capsules, syrups and elixirs and parenterally as solutions, suspensions, dispersions, emulsion, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention.

EXAMPLE 1

4-Amino-6,7-dimethoxy-2-[4-(5-ethoxycarbonylamino-1,2,3-thiadiazole-4-carbonyl)-piperazin-1-vl]-quinazoline Hydrochloride A solution of 5-ethoxycarbonylamino-1,2,3-thiadiazole-4-carbonyl chloride (5.17 g., 0.022 mole) in dioxane (35 ml. was added to a solution of 4-amino-6,7-dimethoxy-2-(1-piperazinyl)quinazoline (6.35 g., 0.022 mole) in dioxane (190 ml.). The resultant mixture was stirred at reflux for 1 hour, and then at 23° C. for 18 hours. Filtration gave the title compound; m.p. 281°–284° C. (dec.) after crystallization from methanol.

Anal. Calcd for $C_{20}H_{24}N_8O_5S \cdot HCl$: C, 45.76; H, 4.80; Cl, 6.75; N, 21.35. Found: C, 45.49; H, 4.65; Cl, 7.10; N, 21.06.

The 5-ethoxycarbonylamino-1,2,3-thiadiazole-4-carbonyl chloride starting material was obtained in the following manner.

A. 5-Ethoxycarbonylamino-1,2,3-thiadiazole-4-carboxylic Acid. A suspension of sodium thiocyanate (24.30 g, 0.30 mole) in acetonitrile (120 ml), maintained at 19° C., was treated dropwise over 22 minutes with a solution of ethyl chloroformate (28.7 ml, 0.30 mole) in acetonitrile (25 ml). The resultant mixture was stirred for 25 minutes at 20° C. and then ethyl diazoacetate (31.5 ml, 0.30 mole) was added. After stirring for 24 hours, 6.0 N hydrochloric acid (300 ml) was added with cooling. Acetonitrile solvent was removed in vacuo and the residual aqueous suspension was extracted several times with ether. Combined ether extracts were washed with water, dried ($Na_2SO_4$) and evaporated to leave 51.0 g of ethyl 5-ethoxy-carbonylamino-1,2,3-thiadiazole-4-carboxylate. This ester was hydrolyzed by refluxing for 6 hours in a mixture of ethanol (80 ml) and aqueous 6 N hydrochloric acid (400 ml) to yield the title acid; m.p. 179°–180° dec. after crystallization from nitromethane.

B. 5-Ethoxycarbonylamino-1,2,3-thiadiazole-4-carbonyl Chloride. Oxalyl chloride (8.76 g, 0.069 mole) was added slowly to a stirred suspension of 5-ethoxycarbonylamino-1,2,3-thiadiazole-4-carboxylic acid (5.00 g, 0.023 mole) in dry ether (65 ml) containing three drops of N,N-dimethylformamide. Teterahydrofuran was added and the resultant clear solution was stirred at 23° C. for 2 hours. Filtration and subsequent evaporation gave a residue which was triturated under petroleum ether to yield the title acid chloride (5.17 g, 96%), m.p. 129°–133.5° C.

EXAMPLE 2

4Amino-6,7-dimethoxy-2-[4-(1,2,3-thiadiazole-4-carbonyl)piperazin-1-yl]quinazoline Hydrochloride The title compound was prepared by reacting 1,2,3-thiadiazole-4-carbonyl chloride (D. L. Pain and R. Slack, J. Chem. Soc., 5166 (1965)) and 4-amino-6,7-dimethoxy-2-(1-piperazinyl) quinazoline according to the procedure of Example 1. After crystallization from aqueous ethanol, the title compound melted at 270° C. (dec.).

Anal. Calcd for $C_{17}H_{19}N_7O_3S \cdot HCl$: C, 46.62; H, 4.60; N, 22.39; S, 7.32. Found: C, 46.43; H, 4.39; N, 22.58; S, 7.14 (corrected for 6.08% water of hydration).

EXAMPLE 3

4-Amino-6,7-dimethoxy-2-[4-(1,2,3-thiadiazole-5-carbonyl)piperazin-1-yl]quinazoline Hydrochloride A solution of potassium hydroxide (3.30 g.) in water (7 ml.) was added to a solution of ethyl 1,2,3-thiadiazole-5-carboxylate (8.00 g.) in ethanol (25 ml.). The mixture was stirred at 23° C. for 2 hours, and then was worked up to yield potassium 1,2,3-thiadiazole-5-carboxylate. A suspension of this salt (3.00 g.) in toluene (25 ml.) was treated at 0° C. with oxalyl chloride (1.6 ml.), stirred at 0° C. for 1 hour, and then was worked up to yield 1,2,3-thiadiazole-5-carbonyl chloride.

Reaction of 1,2,3-thiadiazole-5-carbonyl chloride and 4-amino-6,7-dimethoxy-2-(1-piperzinyl)quinazoline according to the procedure of Example 1 provided the title compound having a melting point of 295°–297° C. after crystallization from aqueous ethanol.

Anal. Calcd for $C_{17}H_{19}N_7O_3S \cdot HCl$: C, 46.62; H, 4.60; N, 22.39; S, 7.32. Found: C. 46.91, H, 4.51; N, 21.91; S, 7.39 (corrected for 2.6% water of hydration).

EXAMPLE 4

4-Amino-6,7-dimethoxy-2-[4-(5-methyl-1,2,3-thiadiazole-4-carbonyl)-piperizin-1-yl]-quinazoline Hydrochloride Hydrolysis of ethyl 5-methyl-1,2,3-thiadiazole-4-carboxylate (D. L. Pain and R. Slack, J. Chem. Soc., 5166 (1965)) and subsequent treatment of the acid with oxalyl chloride according to the method of Example 3 provides 5-methyl-1,2,3-thiadiazole-4-carbonyl chloride.

Reaction of the carbonyl chloride and 4-amino-6,7-dimethoxy-2-(1-piperizinyl)-quinazoline according to the procedure of Example 1 provides the title compound.

We claim:

1. A process for treating hypertension which comprises systemically administering to a mammal in need of said treatment an antihypertensive effective amount of a compound having the formula

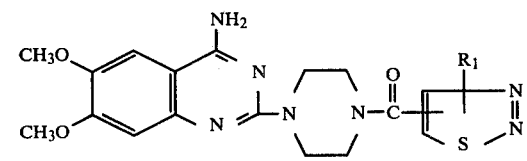

or a pharmaceutically acceptable salt thereof wherein
$R_1$ is hydrogen, amino, lower alkyl of 1 to 4 carbon atoms inclusive, or $NHCO_2R_2$ in which $R_2$ is lower alkyl of 1 to 4 carbon atoms inclusive.

2. The process of claim 1 wherein said compound is 4-amino-6,7-dimethoxy-2[4-(5-ethoxycarbonylamino-1,2,3-thiadiazole-4-carbonyl)-piperazin-1-yl]quinazoline.

3. The process of claim 1 wherein said compound is 4-amino-6,7-dimethoxy-2[4-(5-ethoxycarbonylamino-1,2,3-thiadiazole-4-carbonyl)-piperazin-1-yl]quinazoline hydrochloride.

* * * * *